United States Patent [19]

Knevels

[11] Patent Number: 4,893,516

[45] Date of Patent: Jan. 16, 1990

[54] METAL CONTACT MEMBER FOR A MEASURING LANCE FOR TAKING MEASUREMENTS IN METAL MELTS

[75] Inventor: Johan M. J. Knevels, Bree, Belgium

[73] Assignee: Electro-Nite International NV, Antwerpen, Netherlands

[21] Appl. No.: 304,982

[22] Filed: Jan. 31, 1989

[30] Foreign Application Priority Data

Feb. 17, 1988 [DE] Fed. Rep. of Germany ..... 38048809

[51] Int. Cl.$^4$ ............................................... C21B 7/24
[52] U.S. Cl. .................................. 73/866.5; 277/116.2
[58] Field of Search ......................... 73/866.5, DIG. 9; 277/102, 116.2, 116.4, 116.6; 285/138–143; 266/99; 174/77 R

[56] References Cited

U.S. PATENT DOCUMENTS

| | | | |
|---|---|---|---|
| 1,988,397 | 1/1935 | Reed | 277/116.6 |
| 3,233,202 | 2/1966 | Kyle | 174/77 R |
| 3,455,164 | 7/1969 | Boyle | 73/DIG. 9 |
| 3,463,005 | 8/1969 | Hance | 374/140 |
| 4,377,289 | 3/1983 | Lefebvre | 277/116.4 |
| 4,438,653 | 3/1984 | Beentjes | 374/140 |
| 4,645,243 | 2/1987 | Bucher et al. | 285/138 |
| 4,778,281 | 10/1988 | Falk | 374/140 |

FOREIGN PATENT DOCUMENTS 2842136 10/1979 Fed. Rep. of Germany ........ 266/99

Primary Examiner—Robert R. Raevis
Attorney, Agent, or Firm—Panitch, Schwarze, Jacobs & Nadel

[57] ABSTRACT

A metal contact member for a measuring lance for taking measurements in metal melts, said contact member consisting of two tubes (10, 11) interconnected by a tapered portion (14) of one tube (11) being pushed into the widened opening (12) of the other tube (10) with the interposition of an insulating member (17) in the form of a sleeve, a cup-shape insulating member (26) being inserted into the widened interior of the end of the contact member (1) and containing the contact by which the contact member is electrically connected to the measuring probe. The sleeve-shaped insulating member (17) is sealed off from the wall of the widened portion (12) of the tube (10) and the wall of the tapered portion (14) of the tube (11) of the contact member by the insertion of annular seals (21) while sealing of the cup-shaped insulating member (26) from the wall of the widened interior of the tube end connected to the probe is provided by another annular seal (30).

8 Claims, 2 Drawing Sheets

METAL CONTACT MEMBER FOR A MEASURING LANCE FOR TAKING MEASUREMENTS IN METAL MELTS

BACKGROUND OF THE INVENTION

The invention relates to a metal contact member which is disposed at the bottom end of a measuring lance and onto which a consumable probe can be fitted to make an electrical connection, said probe containing measuring means for taking measurements in metal melts, the contact member consisting of two tubes interconnected by a tapered portion of one tube being pushed into the widened opening of the other tube with the interposition of an insulating member in the form of a sleeve, the outer wall portions of the two tubes abutting a flange of the insulating member having the same outside diameter as the contact member, and a cup-shaped insulating member being inserted into the widened interior of the end of the contact member which is electrically connected to the probe, the cup-shaped insulating member interior containing contacts which are insulated from one another and which are connected, through the base of the insulating member, to leads taken out through the contact member.

Measuring lances of this kind are used to determine oxygen activity and/or the temperature of steel melts. Incorrect measurements and divergent measurement results for which there was initially no explanation were found to occur in practice. Exhaustive experiments have shown that the falsification of the measurements is due to water inclusions present in the cardboard protective tubes surrounding the measuring probe and the contact member. On immersion of the probe into the melt the water is liberated and passes through capillary openings between the insulating members and the metal walls of the tubes of the contact member into its interior, which is filled with a filler. Since it is not possible to obtain perfect sealing between the filler and the metal tubes because of the different coefficients of thermal expansion of these parts, the penetrating moisture can, under unfavorable conditions, advance as far as the electrical contacts and falsify the measurements.

The present invention is based on the surprising finding referred to above, which has been confirmed by the experimental results. The object of the invention is so to devise and seal the contact member disposed on the measuring lance as to obviate falsification of the measurements due to penetrating moisture.

Starting from a metal contact member of the type described in the preamble, according to the invention, the sleeve-shaped insulating member is sealed from the wall of the widened portion of one tube and from the wall of the tapered portion of the other tube of the contact member and the cup-shaped insulating member is sealed from the wall of the widened interior of the tube end connected to the probe by the insertion of annular seals.

SUMMARY OF THE INVENTION

Briefly stated, the present invention comprises a metal contact member for disposal at the end of a measuring lance. The contact member has an end adapted to receive a consumable probe so as to electrically connect the probe to leads running through the contact member. The probe contains measuring means for taking measurements in metal melts. The contact member comprises two tubes, one tube having a tapered portion and the other tube having a widened opening portion. A sleeve-shaped insulating member is interposed between the tapered portion of the one tube and the widened portion of the other tube. The insulating member includes a flanged portion which abuts against outer walls of the two tubes. The flanged portion has substantially the same outside diameter as the insulating member at the flanged portion. A cup-shaped insulating member is inserted into the interior of the end of the contact member. The cup-shaped insulating member has a base and an interior, the interior containing contacts which are insulated from one another and are connected, through the base, to the leads. Means are included for providing a watertight seal between the sleeve-shaped insulating member and the tapered portion of the one tube and between the sleeve-shaped insulating member and the widened portion of the other tube. Means are also included for providing a watertight seal between the cup-shaped insulating member and the other tube.

BRIEF DESCRIPTION OF THE DRAWINGS

The foregoing summary, as well as the following detailed description, will be better understood when read in conjunction with the appended drawings. For the purpose of illustrating the present invention, there is shown in the drawings an embodiment which is presently preferred, it being understood, however, that this invention is not limited to the precise arrangements and instrumentalities shown.

In the drawings.

DESCRIPTION OF PREFERRED EMBODIMENT

In a preferred embodiment of the invention, the contact member is constructed as follows:

(a) The tapered portion of one tube of the contact member and the widened portion of the other tube are provided with stepped shoulders which form peripheral abutment surfaces;

(b) The sleeve-shaped insulating members contain stepped recesses disposed at appropriate places to form peripheral radial abutment surfaces situated opposite those of the tubes, sealing rings of elastic material being disposed between the opposite abutment surfaces and being clamped when the two tubes of the contact member are fitted inside one another;

(c) At its end facing the interior of the tube, the base of the cup-shaped insulating member contains a stepped peripheral recess situated opposite a corresponding stepped shoulder in the inner wall of the tube, two opposite radial abutment surfaces being formed, between which a sealing ring of elastic material is clamped on insertion of the cup-shaped insulating member into the tube end.

Advantageously, the tube connected to the lance holder has the widening in the region of its bottom portion and the tube to which the measuring probe is connectable has the tapered portion at its top In another advantageous embodiment of the invention, the base of the cup-shaped sleeve is provided with two cylindrical projections which extend into the cavity of the tube and which have longitudinal bores extending into the interior of the sleeve, the leads connected to the contact socket and contact pin are taken through bores in the projections and each entry aperture is covered by a shrink tube which bears sealingly against the lead and the cylindrical projection.

It has also been found advantageous if the top portion of the tube adjacent the lance is filled with a silicone material to replace the filler material conventionally used here.

Figure 1:
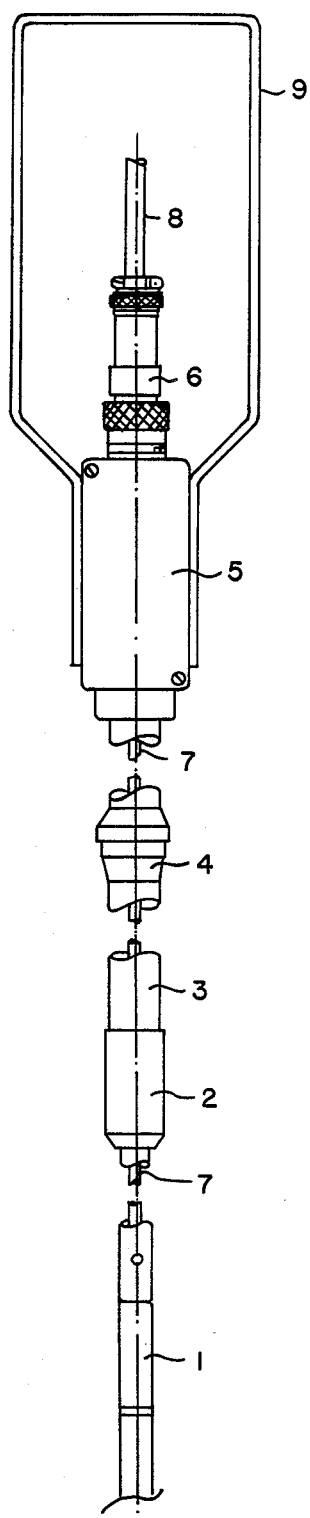
FIG. 1 is a diagram showing an immersion measuring lance.

The immersion measuring lance shown in FIG. 1 consists of a lance holder 2, a steel tube 3, an abutment member 4, and a handle 9. The cable 7, which is insulated from the continuous internal bore through which it passes, is connected, at the top end of the lance, via a quick plug-in connection 6, to the outer cable 8 leading to the measuring instruments, while the bottom end is connected to a contact member 1, which is fixed to the lance holder 2 and the special construction of which is the subject of the invention. An electrical contact, to which an interchangeable measuring probe, e.g., for measuring the oxygen activity and/or the temperature of a metal melt, can be detachably electrically connected, is mounted at the end of the contact member 1. Both the measuring probe and the contact sleeve are surrounded by one or more protective tubes (not shown) which usually consist of cardboard. The outer cardboard tube surrounding the contact member 1 can extend over the lance holder 2 as far as the abutment member 4.

Figure 2:
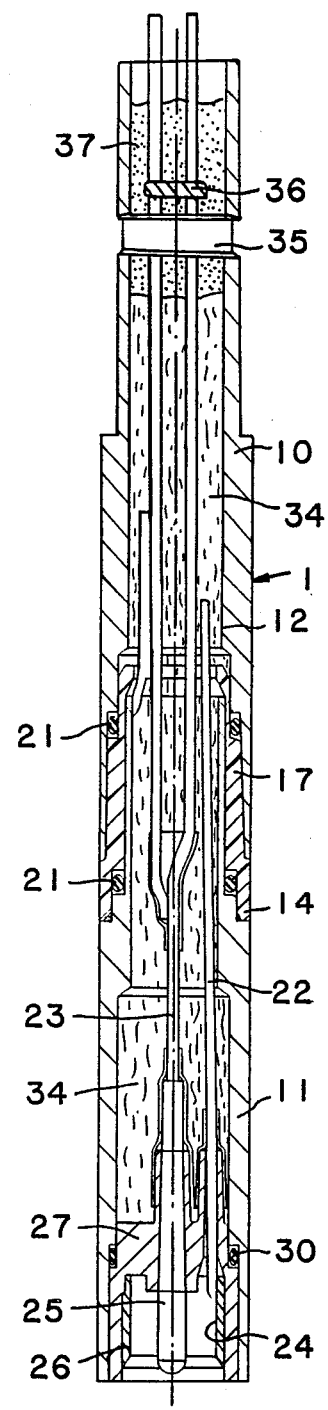
FIG. 2 is a longitudinal section through the contact member.
Figure 3:
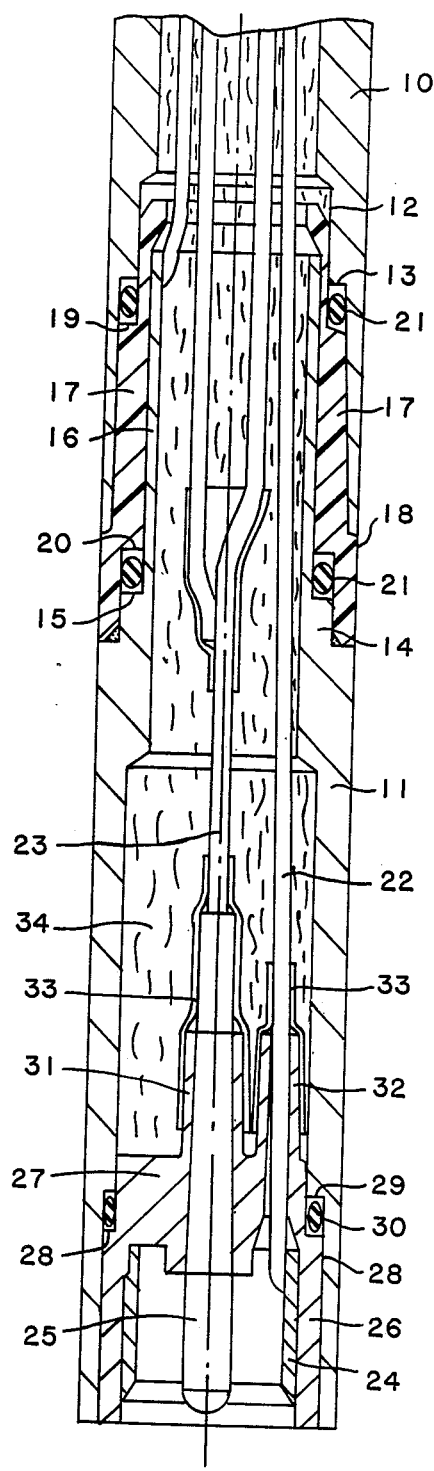
FIG. 3 is a longitudinal section through the bottom part of the contact member to an enlarged scale.

As will be seen from FIGS. 2 and 3, the contact member 1 comprises two cylindrical metal tubes 10 and 11 disposed consecutively and interconnected by plugging into one another. The top tube 10 on the lance side is electrically connected to the measuring probe. In the region of its bottom end, the cavity of the tube 10 is widened out and the widened portion 12 is provided with a stepped shoulder 13 extending in the peripheral direction to form a peripheral radial abutment surface. The top end of the tube 11, which has the same outside diameter as the tube 10, is tapered, the tapered portion 14 is provided with a shoulder 15 which forms a stepped reduction of the diameter thereof to form a peripheral radial abutment surface. The portion 16 situated above the shoulder has a smaller outside diameter than the widened interior of the tube 10. The tubes 10 and 11 are interconnected by fitting one inside the other with the interposition of an insulating member 17 in the form of a sleeve extending in the region of the overlapping ends of the tubes 10 and 11. The insulating member has a bottom flange 18 having the same outside diameter as the tubes of the contact member 1, the ends of the tubes abutting thereagainst. According to the invention, the insulating member 17 has stepped recesses 19 and 20, which correspond to the stepped shoulders 13 and 15 of the tubes 10 and 11, and are so disposed that the abutment surfaces they form are situated opposite those of the contact member tubes. Sealing rings 21, e.g., O-rings of elastic material, are inserted between the opposite abutment surfaces and, when the tubes are fitted one inside the other, are compressed and clamped against the surrounding walls. The penetration of moisture through capillary openings between the metal parts of the contact member and the insulating member is thus avoided by simple means.

As will be seen from FIG. 2, two of the four measuring leads which pass out through the contact sleeve and the measuring lance and are connected to the measuring instruments, i.e., the leads 22 and 23, are electrically connected to a contact consisting of a contact socket 24 and a contact pin 25. The contact is disposed in the interior of a cup-shaped sleeve 26 of insulating material which is pushed into and fastened in the bottom end of the contact member tube 11 facing the measuring probe. The contact pin 25 extends centrally through the base 27 of the insulating sleeve 26 while the contact socket 24 consists of a metal liner which covers the lateral inner wall of the sleeve 26.

In order to avoid moisture penetration at this point as well, the base 27 of the cup-shaped sleeve 26 is provided with a stepped inwardly extending peripheral recess 28 at the end facing the cavity of the tube 11, said recess being situated opposite a stepped shoulder 29 in the inner wall of the tube 11. A sealing ring 30 of elastic material is inserted between the resulting radial abutment surfaces and is clamped when the cup-shaped sleeve is inserted (FIG. 3).

In a preferred embodiment of the invention, the base 27 of the cup-shaped sleeve 26 is provided with two cylindrical projections 31 and 32 extending into the cavity of the tube 11 and formed with longitudinal bores which extend into the interior of the sleeve. The projection 31 is disposed centrally and serves to accommodate a lengthened part of the contact pin 25 while the second cylindrical projection 32 is disposed eccentrically and serves to feed the lead 22 to the contact socket 24. According to the invention, a shrink tube 33 covers part of the leads 22 and 23 before they enter the cylindrical projections 31 and 32, said tube fitting sealingly against the leads and also being drawn sealingly over the cylindrical projections.

The cavity 34 of the tubes 10 and 11 is conventionally filled with a filler consisting of a two-component epoxy resin. Reference 35 denotes a mandrel, reference 36 a spacer plate formed with four apertures by means of which the leads can be kept spaced part. It has also been found advantageous to fill a portion 37 of the cavity of the end of the tube 10 adjacent the lance extending substantially as far as the mandrel 35 with a silicone material which prevents the penetration of moisture to the top end of the contact member. The use of a silicone material instead of a conventional filler is possible in this region because the top end of the contact member heats up less than the middle and bottom portions thereof.

I claim:

1. A metal contact member for disposal at an end of a measuring lance, said contact member having an end adapted to receive a consumable probe so as to electrically connect said probe to leads running through said contact member, said probe containing measuring means for taking measurements in metal melts, the contact member comprising two tubes, one tube having a tapered portion and the other tube having a widened opening portion, a sleeve-shaped insulating member interposed between said tapered portion of said one tube and said widened portion of said other tube, said insulating member having a flanged portion, the two tubes having outer wall portions abutting said flanged portion of the insulating member and having substantially the same outside diameter as the insulating member at said flanged portion, and a cup-shaped insulating member forming a part of the interior of said end of the contact member, the cup-shaped insulating member having a base and an interior, said interior of the cup-shaped member containing contacts which are insulated from one another and which are connected, through the base of the cup-shaped insulating member, to said leads, first means (21) for providing a water-tight seal between said sleeve-shaped insulating member (17) and the tapered portion (14) of said one tube (11) and between said sleeve-shaped insulating member and the widened portion (12) of said other tube (10), and second means (30) for providing a watertight seal between said cup-shaped insulating member (26) and said one tube.

2. The metal contact member according to claim 1, wherein the tapered portion (14) of said one tube (11) and the widened portion (12) of said other tube (10) are provided with stepped shoulders (13, 15) which form peripheral radial abutment surfaces, and the sleeve-shaped insulating member (17) contains stepped surfaces (19, 20) disposed so as to form peripheral radial abutment surfaces facing those of the tubes, and wherein said first means for providing a water-tight seal comprises sealing rings (21) of elastic material disposed between said facing abutment surfaces.

3. The metal contact member according to claim 1, wherein the base (27) of the cup-shaped insulating member (26) contains a stepped peripheral surface (28) situated opposite a corresponding stepped surface (29) in the inner wall of said one tube (11), two opposite radial abutment surfaces being formed thereby, and wherein said second means for providing a water-tight seal comprises a sealing ring (30) of elastic material clamped between the cup-shaped insulating member and said one tube.

4. The metal contact member according to claim 3, including a lance holder (2) connected to said other tube (10) and a measuring probe connected to said one tube (11).

5. The metal contact member according to claim 4, wherein the base (27) of the cup-shaped insulating member (26) is provided with two cylindrical projections (31, 32) which extend into said one tube (11), each projection having a longitudinal bore extending therethrough.

6. The metal contact member according to claim 5, including a contact socket (24) and a contact pin (25), said leads (22, 23) being connected to the contact socket (24) and contact pin (25), said leads extending within said bores in the projections (31, 32), and a shrink tube (33) surrounding at least a portion of one of said projections and a portion of one of said leads to thereby seal said last-mentioned projection.

7. The metal contact member according to claim 6, wherein a portion (37) of said one tube (10) is filled with a silicone material.

8. A measuring lance for measuring oxygen or other activity of molten metal, said lance including a contact member for electrical connection to a consumable measuring probe, said contact member comprising first and second metal tubes and a sleeve-shaped insulating member telescopically interconnecting said tubes, said tubes and sleeve-shaped member being configured so as to define one gap between said sleeve-shaped member and one of said tubes and another gap between said sleeve-shaped member and the other of said tubes, and means disposed in each gap for providing a water-tight seal between said sleeve-shaped member and each of said tubes.

* * * * *